United States Patent
Okano et al.

(10) Patent No.: US 7,405,078 B2
(45) Date of Patent: Jul. 29, 2008

(54) BED MATERIAL FOR CELL CULTURE, METHOD FOR CO-CULTURE OF CELL AND CO-CULTURED CELL SHEET OBTAINABLE THEREFROM

(75) Inventors: Teruo Okano, Chiba (JP); Masayuki Yamato, Tokyo (JP); Akihiko Kikuchi, Tokyo (JP)

(73) Assignee: Cellseed Inc., Tokyo (JP)

( * ) Notice: Subject to any disclaimer, the term of this patent is extended or adjusted under 35 U.S.C. 154(b) by 259 days.

(21) Appl. No.: 10/221,751

(22) PCT Filed: Mar. 16, 2001

(86) PCT No.: PCT/JP01/02123

§ 371 (c)(1),
(2), (4) Date: Sep. 16, 2002

(87) PCT Pub. No.: WO01/68799

PCT Pub. Date: Sep. 20, 2001

(65) Prior Publication Data
US 2003/0036196 A1      Feb. 20, 2003

(30) Foreign Application Priority Data
Mar. 16, 2000 (JP) .............................. 2000-074269

(51) Int. Cl.
*C12N 5/00* (2006.01)
*C12N 5/02* (2006.01)

(52) U.S. Cl. ..................................... 435/395

(58) Field of Classification Search ................ 435/325, 435/347, 378
See application file for complete search history.

(56) References Cited

FOREIGN PATENT DOCUMENTS

| EP | 387975 A | 9/1990 |
|---|---|---|
| EP | 470681 A2 * | 2/1992 |
| JP | 4-4869 A | 1/1992 |
| JP | 4-237492 A | 8/1992 |
| JP | 7-75547 A | 3/1995 |

OTHER PUBLICATIONS

Kushida et al, Journal of Biomedical Materials Research; vol. 45, Issue 4, Date: Jun. 1999, pp. 355-362.*
Okano et al, Biomaterials; vol. 16, Issue 4, Date: 1995, pp. 297-303.*
Hirose et al, "(Temperature-Responsive Surface for Novel Co-Culture Systems of Hepatocytes with Endothelial Cells: 2-D Patterned and Double Layered Co-Cultures," (Yonsei Medical Journal), 2000, vol. 41, No. 6, pp. 803-813.*

* cited by examiner

*Primary Examiner*—Jon P Weber
*Assistant Examiner*—Amanda P Wood
(74) *Attorney, Agent, or Firm*—Nixon & Vanderhye P.C.

(57) ABSTRACT

By using a bed material for cell culture having a surface composed of two domains of domain A coated with a temperature-responsive polymer and domain B composed of any one or a combination of a domain coated with a polymer having high affinity with cells, a domain coated with the temperature-responsive polymer in an amount different from the amount of the temperature-responsive polymer of domain A, and a domain coated with a polymer which responds to a temperature different from the temperature to which domain A responds, a method for the co-culture of a plurality of kinds of cells which has heretofore been difficult becomes possible.

9 Claims, 4 Drawing Sheets

BED MATERIAL FOR CELL CULTURE, METHOD FOR CO-CULTURE OF CELL AND CO-CULTURED CELL SHEET OBTAINABLE THEREFROM

This application is the US National Phase of international application PCT/JP01/02123 filed 16 Mar. 2001, which designated the US.

TECHNICAL FIELD

The present invention relates to a bed material for cell culture in the fields of biology, medicine, immunology and the like, and a method for the co-culture of cells by using the substrate material and a method for preparing a cell sheet obtainable by the method.

BACKGROUND ART

Recently, the cell cultures with the purpose of the development of artificial organs and the development of regeneration medicine, safety evaluation, drugs and the like are noted and their techniques are variegated and have become more and more highly advanced. As an example, the co-culture method (coexistent culture) for culturing two or more kinds of cells on the same culture substrate can be mentioned.

Heretofore, cell culture has been conducted on a glass surface or on the surface of a synthetic polymer having been subjected to various treatments. For example, various vessels using polystyrene as the material which have been subjected to the treatment, for example, γ-ray irradiation and silicone coating are widespread as the cell culture vessels but none of them could sufficiently cope with various culture methods.

Japanese Patent Publication (Kokoku) No. Hei 6-104061/1994 describes a novel cell culture method comprising culturing cells on a cell culture substrate whose substrate surface has been coated with a polymer having an upper or lower critical solution temperature to water of 0 to 80° C. at a temperature of not higher than the upper critical solution temperature or not lower than the lower critical solution temperature, and then rendering the culture temperature a temperature of not lower than the upper critical solution temperature or not higher than the lower critical solution temperature to detach the cultured cells without treating with an enzyme. However, with the substrate illustrated herein, a temperature-responsive polymer is uniformly coated on the substrate surface, and accordingly all cultured cells on the substrate surface are detached, and this substrate could not fully cope with a wide variety of culture methods.

Further, it is very difficult to allow a plurality of kinds of cells to proliferate to effect co-culture by using the above described cell culture vessels. For example, co-culture (in consideration of the structure of the liver of the body of living) has been considered to be effective for the long-term culture of hepatocyte but it is impossible to effect the co-culture by simply mixing hepatocyte with fibroblasts or hepatocyte with endothelial cells.

Hepatocyte is by no means singly present in the liver. The liver is composed of a repetition of a fine structure of a so-called hepatic lobule which endothelial cells, stellate cells and the like in addition to the hepatocyte constitutes. Co-culture has been examined on the basis of the thought that hepatic nonparenchymal cells are important for the maintenance of the function of hepatocyte. Further, also from the observation that the hepatic differentiation function can be better maintained when hepatic nonparenchymal cells are included, the necessity of hepatic nonparenchymal cells are strongly suggested when the primary hepatocyte is incorporated into an artificial liver module. However, the method using conventional dishes realizes only an ultrashort-term co-culture alone and, in addition, except for the variation in the ratio of the number of both kinds of cells, a sufficient examination could not be done and the details could not be clarified.

Toner et al. fixed laminin in the form of a pattern on a silicone surface by irradiation with rays with the use of the photoresist technique [S. N. Bhatia, M. L. Yarmush and M. Toner, J. Biomed. Mater. Res., 34, 189-199 (1997)]. When hepatocyte was cultured on this surface, they attached only to the laminin-fixed domain to proliferate. Then, when fibroblasts were seeded, they attached on to the silicone domain due to their very high adhesion to achieve a co-culture system with the hepatocyte. However, any combination could not achieve the co-culture system, and the co-culture of hepatocyte with endothelial cells having not so high adhesion as that of fibroblast could not be achieved.

Japanese Patent Publication (Kokai) No. Hei 4-94679/1992 developed the technology as illustrated in the above described Japanese Patent Publication (Kokoku) No. Hei 6-104061/1994 and described a method for culturing cells with the use of a substrate whose surface has been coated with a temperature-responsive polymer in the form of a pattern. However, the substrate as illustrated herein had weak cell affinity for its surface to which the temperature-responsive polymer had not attached, and was insufficient as the substrate for culturing a plurality of kinds of cells. As long as this substrate was used, it was impossible to detach an entire cell sheet extending over the substrate surface after the co-culture.

DISCLOSURE OF INVENTION

The present invention has an object to provide a bed material for cell culture which can cope with various cell culture methods. Further, the present invention has been achieved to solve the above described problems by using this substrate material and has an object to provide a method for the co-culture of cells which enables, for example, the co-culture of cells such as endothelial cells having no high adhesion with other cells such as hepatocyte and a method for preparing a cell sheet thereby.

The present invention relates to a bed material for cell culture having a temperature-responsive domain on its surface.

Further, the present invention relates to a method for the co-culture of cells which comprises using a bed material for cell culture having a temperature-responsive domain on its surface.

Still further, the present invention relates to a method for preparing a cell sheet which comprises using a bed material for cell culture having a temperature-responsive domain on its surface.

BRIEF DESCRIPTION OF DRAWINGS

FIG. 1a is a mask pattern of a metallic mask used. The pore diameter is 1 mm and the distance between the centers of two pores is 1.5 mm. FIG. 1b is a microscopic photograph when hepatocyte was seeded at 37° C. The hepatocyte adhered and extended all over the surface. FIG. 1c is a microscopic photograph after the hepatocyte on N-isopropyl acrylamide polymer (PIPAAm) was detached at 20° C. The cells are detached only from the temperature-responsive domain having been grafted with the PIPAAm. FIG. 1d is a microscopic photograph of the mask pattern three days after the endothelial cells were seeded at 37° C. The hepatocyte and the endothelial cells could stably have been co-cultured in accordance with the mask pattern.

FIG. 2a shows the state of the secretion after culturing for 13 days; FIG. 2b shows the position of the cell nuclei at that time (the positions of the cells in FIG. 2a and FIG. 2b being made the same); FIG. 2c shows when the culture was continued for 22 days as it was without detaching the cells from the bed material for cell culture; and FIG. 2d shows the position of the cell nuclei at that time (the positions of the cells in FIG. 2c and FIG. 2d being made the same). It could be understood that by continuing the culture without detaching the cells, the amount of secretion is sharply reduced.

FIG. 3 shows the state that after culturing for 13 days, the cells were detached and allowed to reattach on to the bed material for cell culture by the method of the present invention, and FIG. 3a shows the state when the culture was further continued for 30 days after the detachment of the cells, and FIG. 3c shows the state when the culture was further continued for 60 days after the detachment of the cells. It could be understood that according to the present invention the activity of the alveolar epithelial cells can be retained for a long period of time.

FIG. 4a is the result of subjecting the specific sugar chain of the surface layer of the alveolar epithelial cells after the culture for 13 days to fluorescence stain according to the conventional method. FIG. 4b is the result when the cells were detached and then allowed to reattach on to the bed material for cell culture, and it could be understood that the alveolar epithelial cells have clearly been activated by the above described method.

BEST MODE FOR CARRYING OUT THE INVENTION

The substrate material to be illustrated by the present invention is characterized by having, on its surface, two domains of domain A coated with a temperature-responsive polymer and domain B composed of any one or a combination of any two or three of (1) a domain coated with a polymer having high affinity with cells, (2) a domain coated with the temperature-responsive polymer in an amount different from the amount of the temperature-responsive polymer of domain A, and (3) a domain coated with a polymer which responds to a temperature different from the temperature to which domain A responds.

Its preparation method is by no means limited as long as the substrate material finally has the above described structure and, for example, methods including (a) a method comprising first preparing domain B on the entire surface of a substrate material, and then masking the portions which finally come to domain B to place domain A thereon or the method by reversing the order of the preparation of domains A and B, (b) a method comprising first preparing domain B on the entire surface of a substrate material, and then spraying a substance which finally constitutes domain A on to domain B to place domain A thereon or the method by reversing the order of the preparation of domains A and B, (3) a method comprising previously dispersing or emulsifying coating materials in a solvent, respectively, and coating the resulting dispersions or emulsions, respectively, (4) a method comprising previously preparing two layers of domains A and B, and scraping off either layer with ultrasonic waves or by scanning equipment, and (5) a method comprising subjecting coating materials to offset printing, respectively, can be used singly or jointly.

The forms of the coating area, observed from above, include, for example, (1) a pattern composed of lines and spaces, (2) a polka-dotted pattern, (3) a checkered pattern, and other patterns of specific shapes or a mixed pattern of these patterns, and are by no means limited.

The size of the coating area is by no means limited. In culturing a plurality of kinds of cells, the longest distance between cells (distance between the centers of two cells) present in the adjoining domains A and B is 1 cm or less, preferably 0.05 mm to 8 mm, more preferably 0.1 mm to 3 mm. When the distance is longer than 1 cm, the influence on different kinds of cells to be co-cultured becomes weak to reduce the co-culture efficiency, and thus such distances are unfavorable. Conversely, when the distance is less than 0.05 mm, there is no sufficient space to allow cells to proliferate in either domain A or domain B or in both domains A and B to unfavorably reduce the co-culture efficiency.

As the material of the cell culture substrate to be provided with coating, not only a substance such as polystyrene and poly(methyl methacrylate) but also a substance normally capable of giving a form including, for example, polymeric compounds except the above described substances, ceramics and metals can be used. The shape is not limited to a cell culture dish such as a petri dish and may be a plate, a fiber, and a (porous) particle. Further, the shape may have a shape of a container (a flask and the like) which is generally used in cell culture and the like.

As the method for coating a temperature-responsive polymer on to the cell culture substrate, a method of bonding a substrate material to a coating substance (1) by chemical reaction or (2) by utilizing physical interaction can be conducted singly or jointly. Namely, (1) in bonding them by chemical reaction, irradiation with electron beams (EB), γ-rays or ultraviolet rays, plasma treatment, corona treatment or the like can be used. Furthermore, when the substrate and the coating material have appropriate reactive functional groups, an organic reaction such as radical reaction, anionic reaction and cationic reaction which are generally used can be utilized. (2) The method by physical interaction includes a method using physical adsorption such as coating and kneading with the use of the coating material alone or together with a matrix having good compatibility with the substrate as the medium (for example, a graft polymer and a block polymer of a monomer which forms a substrate or a monomer which has good compatibility with the substrate with the coating material).

The polymer having high affinity with cells is, for example, the one having an ionic group, a hydrophilic/hydrophobic group and the like, and after coating the substrate surface with the polymer, the coated surface may be subjected to surface treatment with glow discharge, corona discharge or the like, and furthermore the polymer may be any one of cell adhesive proteins such as fibronectin, collagen, and laminin or a combination thereof or may be treated with them, and is not particularly limited.

The bed material for cell culture is normally surface-treated with glow discharge, corona discharge or the like in order to allow cells to easily attach on to the substrate surface. According to the technique of the present invention, by using this surface as domain B, domain A composed of a temperature-responsive polymer may be prepared but with the obtained bed material for cell culture, some of the cells attaching to domain B are dragged to be detached when the cells of domain A are detached as will be described below to unfavorably reduce efficiency. In this instance, it has been found that by strengthen the attachability of the cells of the domain B, such a problem can be solved.

The coating amount of the temperature-responsive polymer is suitably in the range of 0.1 to 5.0 $\mu g/cm^2$, preferably 0.3 to 3.0 $\mu g/cm^2$, more preferably 0.5 to 2.5 $\mu g/cm^2$. With amounts coated of less than 0.1 $\mu g/cm^2$, the cells on the polymer are hard to detach even by varying the temperature and become remarkably inferior in the working efficiency and such amounts are unfavorable. Conversely, with amounts of greater than 5.0 $\mu g/cm^2$, cells are hard to attach on to its domain and it becomes difficult to fully culture the cells.

When a temperature-responsive polymer is allowed to attach on to both domains A and B, it is necessary that the difference in the amount coated between domains A and B is at least 0.10 $\mu g/cm^2$ or more, preferably 0.20 $\mu g/cm^2$ or more, more preferably 0.50 $\mu g/cm^2$ or more. With differences of less than 0.10 $\mu g/cm^2$, when the cells on either of domains A and B are tried to be detached, the cells on the other domain are dragged to be detached, and thus such differences are disadvantageous.

The coating amount of the polymer can be obtained by, for example, the Fourier transform infrared spectrometric total reflection method (FT-IR-ATR method), the analysis by dyeing the coated domain or dyeing a fluorescent substance, furthermore the surface analysis by measuring the contact angle or the like singly or jointly. When the areas of the domains A and B are smaller than the analyzable range, it is necessary to obtain the amount coated in the analyzable area beforehand, and coating may be conducted under the same conditions as its conditions.

The temperature-responsive polymer which is used in the preparation of the temperature-responsive domains of the present invention may be either a homopolymer or a copolymer. The basic structural units of the usable temperature-responsive polymer include, for example, (meth)acrylamide compounds such as acrylamide and methacrylamide, N-alkyl substituted (meth)acrylamide derivatives such as N-ethyl acrylamide (the lower critical solution temperature of the homopolymer: 72° C.), N-n-propyl acrylamide (the lower critical solution temperature of the homopolymer: 21° C.), N-n-propyl methacrylamide (the lower critical solution temperature of the homopolymer: 27° C.), N-isopropyl acrylamide (the lower critical solution temperature of the homopolymer: 32° C.), N-isopropyl methacrylamide (the lower critical solution temperature of the homopolymer: 43° C.), N-cyclopropyl acrylamide (the lower critical solution temperature of the homopolymer:45° C.), N-cyclo-propyl methacrylamide (LCST:60° C.), N-ethoxyethyl acrylamide (the lower critical solution temperature of the homopolymer: 35° C.), N-ethoxyethyl methacrylamide (the lower critical solution temperature of the homopolymer: about 45° C.), N-tetrahydrofurfuryl acrylamide (the lower critical solution temperature of the homopolymer: 28° C.), and N-tetrahydrofurfuryl methacrylamide (LCST: 35° C.), N,N-dialkyl substituted (meth)acrylamide derivatives such as N,N-dimethyl (meth)acrylamide, N,N-ethylmethyl acrylamide (the lower critical solution temperature of the homopolymer: 56° C.], and N,N-diethyl acrylamide (the lower critical solution temperature of the homopolymer: 32° C.), furthermore (meth) acrylamide derivatives having a cyclic group such as 1-(1-oxo-2-propenyl)-pyrrolidine (the lower critical solution temperature of the homopolymer: 56° C.), 1-(1-oxo-propenyl)-piperidine (the lower critical solution temperature of the homopolymer: about 6° C.), 4-(1-oxo-2-propenyl)-morpholine, 1-(1-oxo-2-methyl-2-propenyl)-pyrrolidine, 1-(1-oxo-2-methyl-2-propenyl)-piperidine, and 4-(1-oxo-2-methyl-2-propenyl)-morpholine, vinyl ether derivatives such as methyl vinyl ether (the lower critical solution temperature of the homopolymer: 35° C.), and further when the adjustment of the critical solution temperature depending on the kind of cells to be allowed to proliferate becomes necessary and the enhancement of the interaction between the coating substance and the cell culture substrate is required or with the purpose of adjusting the balance of hydrophilicity and hydrophobicity and the like, copolymers with monomers excluding the above described ones, graft polymers or copolymers of polymers with each other, and mixtures of polymers and/or copolymers may be used. Further, the polymer can also be crosslinked as far as the inherent properties of the polymer are not adversely affected.

When different temperature-responsive polymers are allowed to attach to both domains A and B, respectively, at least 2° C. or more, preferably 4° C. or more, more preferably 8° C. or more are needed for the difference in the temperatures to which respective polymers in domains A and B respond. With differences of less than 2° C., the cells on either temperature-responsive polymer are tried to be detached, the cells on the other temperature-responsive polymer are also dragged and detached, and thus such differences are unfavorable.

The present inventors have developed a novel technique for realizing co-culture by culturing different kinds of cells on a patterned substrate material.

For example, the technique comprises coating a polymer having high affinity with cells on the surface of a substrate as domain B, fixing, as domain A, poly(N-isopropyl acrylamide) (hereinafter referred to as "PIPAAm") in domain B to design a temperature-responsive domain, and utilizing the attachment/detachment of cells on this domain. Namely, the novel technique comprises, for example, first culturing specified cells to a single layer (sheet) at 37° C., then detaching only the cells on the temperature-responsive domain by lowering the temperature (for example, to 25° C. or lower), reraising the temperature to 37° C., and then seeding a different kind of cells to make a domain of the different type of cells in the specified cells which have been rendered a domain and are stable. In the single culture system of hepatocyte, the cells gradually starts dying in a week but according to the method using the bed material for cell culture of the present invention, in the system of hepatocyte and endothelial cells, the co-culture is possible over two weeks or more (at a level of one month), and the function of the hepatocyte (albumin productivity) has been maintained over a long period of time (two weeks or more).

Now, one example of the co-culture method will be explained.

1. Cells are allowed to attach on to the surface of the above described substrate at a temperature of 37° C. and allowed to proliferate. The PPIAAm domain from which the cells can be detached at low temperatures is hydrophobic at 37° C. and changes to be hydrophilic at 32° C. or lower.

2. On this surface a single-layered cell sheet can be prepared. Thus, by using a temperature-responsive polymer to form the temperature-responsive domain into a specific shape, a cell sheet out of which a specified shape has been hollowed can freely be prepared on the surface of the substrate.

3. The temperature-responsive region can freely be designed to form an islands-in-sea structure, a stripe structure or the like, and in a spherical domain having a pore diameter of 0.1 to 0.5 mm or in a stripe domain having a width of 0.1 to 0.5 mm, one kind of cells (hereinafter referred to as "cells A") remains on the portions having not been grafted with the PIPAAm by lowering the temperature (to 25° C. or below).

4. When the temperature is returned to 37° C., cells adhere to the PIPAAm domain, and accordingly another kind of cells (hereinafter referred to as "cells B") can be seeded to allowed to proliferate.

5. The patterns of cells A and cell B can be controlled to become a new system which enables co-culture.

6. When hepatocyte as cells A and endothelial cells as cells B are used, a long-term culture (two weeks or longer) becomes possible by patterning each type of the cells. Further, a long-term functional culture of hepatocyte (for example, continuation of albumin production of 300 ng/h/$10^5$ cells for two weeks or longer) can be conducted. Since a long-term functional culture of hepatocyte is possible, the construction of a testing system of chemical substances by the cultured hepatocyte which is demanded in various fields including, for example, drug development is also possible.

In the present invention, a bed material for cell culture having domain A coated with a temperature-responsive polymer and domain B partly or entirely coated with the temperature-responsive polymer in an amount different from the amount of temperature-responsive polymer of domain A is also illustrated. In this instance, the domain coated with a larger amount of the polymer has quicker responsiveness even at the same temperature. Accordingly, only the cells of one domain are detached by the difference of the treating time. The amount coated may be larger in either of domains A and B in the present invention, and the substrate surface can freely be designed according to the object.

In the present invention, a bed material for cell culture having domain A coated with a temperature-responsive polymer and domain B partly or entirely coated with a polymer which responds to a temperature different from the temperature of the polymer of domain A is also illustrated. In this instance, only the cells on one domain are detached depending on the temperatures to which respective polymers respond. The responsive temperature of either of domains A and B may be higher in the present invention, and the substrate surface can freely be designed according to the object.

Furthermore, when domains A and B are entirely coated with temperature-responsive polymers, all cells co-cultured on the surface of the substrate material as such can be detached by selecting the temperature and the treating time to which all polymers respond.

Further, with domains A and B on the surface of the substrate material entirely coated with temperature-responsive polymers, even when culture is initiated in the mixed state of a plurality of kinds of cells from the beginning, the difference in the adhesion of the cells is caused in the cells having different patterns on the substrate surface, and the cells of the same kind tend to gather with each other to some extent and this tendency has been found to further proceed depending on the temperature treatment. By repeating this operation, the cells which have been difficult to divide can be divided in accordance with the same kind of cells.

According to the bed material for cell culture thus obtained, the co-culture of all cell species is possible since the co-culture method of the present invention, different from the above described Toner method, has no restriction of the combination of cells. For example, the co-culture of alveolar epithelial cells with fibroblasts and intracerebral nerve cells with glial cells can be mentioned.

EXAMPLES

The present invention will now be explained in more detail by giving examples but the present invention is by no means limited thereby.

Examples 1 and 2

On a commercially available polystyrene cell culture dish of FALCON 3002 PETRI DISH (a product of Becton Dickinson Labware Co., Ltd.)(diameter: 6 cm), 0.35 ml of a solution obtained by dissolving an N-isopropyl acrylamide monomer in isopropyl alcohol so as to come to a concentration of 40% was coated. A metallic mask (FIG. 1a) having pores with a diameter of 1 mm and a distance between the centers of two pores of 1.5 mm was placed on the coated surface and irradiated with an electron beam having an intensity of 0.25 MGy in the coated state to fix an N-isopropyl acrylamide polymer (PIPAAm) on the surface of the culture dish in the form of a domain (island portions, the portions under the mask coming to a sea portion which had not been irradiated with the electron beam and had not been coated with the above described monomer). After the irradiation, the culture dish was washed with ion-exchanged water to remove the residual monomer and the PIPAAm not bonded to the culture dish, dried in a clean bench, and sterilized with an ethylene oxide gas to obtain a bed material for cell culture. The amount of the PIPAAm coated in the sea portion was obtained from a bed material for cell culture prepared under the same conditions as described above without using the mask. As the result, it was found that under these conditions 1.6 µg/cm$^2$ of the temperature-responsive polymer was coated on the substrate surface. Before culturing cells, 2 ml of a fibronectin solution having a concentration of 1.5 µg/cm$^2$ (Example 1) or 2 ml of a collagen solution having a concentration of 1.5 µg/cm$^2$ (Example 2) was introduced into the above described culture dish and adsorbed only on the sea portion by incubation at 20° C. for one hour (the PIPAAm portion being hydrophilic at 20° C. and the adhesive protein not being adsorbed thereon) to obtain a bed material for cell culture of the present invention.

On the obtained the bed material for cell culture, bovine aortic vascular endothelial cells were cultured by the conventional method [medium used: a Dulbecco modified Eagle's medium (DMEM) containing 10% of bovine fetal serum, 37° C. under 5% of $CO_2$]. The results of the culture are shown in Table 1.

Examples 3 and 4

Bed materials for cell culture were obtained in the same manner as in Example 1 except that a metallic mask having a diameter of 0.5 mm and a distance between the centers of two pores of 0.8 mm (Example 3) and a metallic mask having a diameter of 1.5 mm and a distance between the centers of two pores of 5 mm (Example 4) were used, respectively.

On the obtained the bed materials for cell culture, bovine aortic vascular endothelial cells were cultured in the same manner as in Examples 1 and 2. The results of the culture are shown in Table 1.

Examples 5 and 6

On the above described FAlCON 3002 PETRI DISH (diameter: 6 cm), 0.35 ml of a solution obtained by dissolving an N-isopropyl acrylamide monomer in isopropyl alcohol so as to come to a concentration of 35% was coated, and then irradiated with an electron beam having an intensity of 0.25 MGy in the coated state to coat an N-isopropyl acrylamide polymer (PIPAAm) on the entire surfaces of the culture dish. Further, 0.35 ml of a 10% isopropyl alcohol solution (Example 5) or a 20% isopropyl alcohol solution (Example 6) of an N-isopropyl acrylamide was coated thereon, and then on the coated surface, a metallic mask (FIG. 1a) having pores having a diameter of 1 mm and a distance between the centers of two pores of 1.5 mm was placed and irradiated with an electron beam having an intensity of 0.25 MGy to coat an N-isopropyl acrylamide polymer (PIPAAm) in a larger amount in the form of a domain (island portions). After the irradiation, a bed material for cell culture was obtained though the steps of washing, drying, and sterilization in the same manner as in Examples 1 and 2. Herein, the amount of the PIPAAm coated in this sea portion was obtained in the same manner as in Examples 1 and 2 and found to be 1.6 $\mu g/cm^2$. In the same manner, the amounts coated in the island portions were 1.8 $\mu g/cm^2$ (Example 5) and 2.0 $\mu g/cm^2$ (Example 6), respectively.

On the obtained the bed material for cell culture, bovine aortic vascular endothelial cells were cultured in the same manner as in Examples 1 and 2. The results of the culture are shown in Table 1.

Comparative Example 1

On the above described PETRI DISH (diameter: 6 cm), 0.35 ml of a 35% isopropyl alcohol of an N-isopropyl acrylamide monomer was coated, and then irradiated with an electron beam having an intensity of 0.25 MGy in the coated state to coat an N-isopropyl acrylamide polymer (PIPAAm) on the entire surface of the culture dish. Then, 0.35 ml of a 40% isopropyl alcohol solution of an N-isopropyl acrylamide monomer was further coated thereon. Subsequently, on the coated surface, a metallic mask (FIG. 1a) having pores having a diameter of 1 mm and a distance between the centers of two pores of 1.5 mm was placed and irradiated with an electron beam having an intensity of 0.25 MGy to coat an N-isopropyl acrylamide polymer (PIPAAm) in a larger amount in the form of a domain (island portions). After the irradiation, a bed material for cell culture was obtained through the steps of washing, drying, and sterilization in the same manner as in Examples 1 and 2. The amounts of the PIPAAm coated in the sea portion and the island portions were obtained in the same manner as in Examples 1 and 2 and found to be 1.6 $\mu g/cm^2$ and 5.5 $\mu g/cm^2$, respectively.

On the obtained the bed material for cell culture, bovine aortic vascular endothelial cells were cultured in the same manner as in Examples 1 and 2. The result of the culture is shown in Table 1.

Comparative Example 2

A bed material for cell culture was obtained by the same means as in Comparative Example 1 except that at the time of the first irradiation, 0.35 ml of a 60% isopropyl alcohol solution of an N-isopropyl acrylamide monomer was coated, and then irradiated with an electron beam having an intensity of 0.4 MGy in the coated state. The amounts of the PIPAAm coated in the sea potion and the island portions were obtained and found to be 5.3 $\mu g/cm^2$ and 8.9 $\mu g/cm^2$, respectively.

On the obtained the bed material for cell culture, bovine aortic vascular endothelial cells were cultured in the same manner as in Examples 1 and 2. The result of the culture is shown in Table 1.

Example 7

A metallic mask having pores in the form of lines having a width of 1 mm and intervals of 1 mm was placed on the above described PETRI DISH (with a marking in the placed position), and 0.35 ml of a 35% isopropyl alcohol solution of an N-n-propyl acrylamide monomer was coated thereon, and then irradiated with an electron beam having an intensity of 0.25 MGy. After the irradiation, washing and drying were conducted in the same manner as in Examples 1 and 2 to first prepare a substrate coated with a polymer in the form of a lattice. Subsequently, the mask was placed so as to slide the pores in the form of a line in 1 mm (the previously masked portions coming to pores). Now, 0.35 ml of a 35% isopropyl alcohol solution of an N-isopropyl acrylamide monomer was coated thereon and irradiated with an electron beam having an intensity of 0.25 MGy to alternately coat an N-n-propyl acrylamide polymer and an N-isopropyl acrylamide polymer in the form of lines. After the irradiation, through the steps of washing and drying, and sterilization in the same manner as in Examples 1 and 2, a bed material for cell culture was obtained. The amounts of each polymer coated were obtained in the same manner as in Examples 1 and 2 and found to be both 1.6 $\mu g/cm^2$.

On the obtained the bed material for cell culture, bovine aortic vascular endothelial cells were cultured in the same manner as in Examples 1 and 2. The results of the culture are shown in Table 1.

Examples 8 and 9

The entire surface of the culture dish was coated with each polymer in the same manner as in Examples 5 and 6 except that on the above described PETRI DISHES (diameter: 6 cm), 0.35 ml of a 30% isopropyl alcohol solution of an N-n-propyl acrylamide monomer (Example 8) or an N-tetrahydrofurfuryl methacrylamide monomer (Example 9) were coated, and subsequently a 10% isopropyl alcohol solution of an N-isopropyl acrylamide monomer was further coated thereon in the same manner as in Example 5 to coat an N-isopropyl acrylamide polymer (PIPAAm) in a larger amount in the portions coated with the above described polymer in the form of a domain. After the irradiation, a bed material for cell culture was obtained through the steps of washing, drying, and sterilization in the same manner as in Examples 1 and 2. The amounts of the PIPAAm coated in the sea portion and the island portions were obtained in the same manner as in Examples 1 and 2, and found to be 1.5 $\mu g/cm^2$ and 2.0 $\mu g/cm^2$, respectively (the same results obtained as in both Examples 8 and 9).

On the obtained bed material for cell culture, bovine aortic vascular endothelial cells were cultured in the same manner as in Examples 1 and 2. The results of the culture are shown in Table 1.

TABLE 1

| | State When Cells Are Cultured | |
|---|---|---|
| | Cell Attachability | Cell Proliferation |
| Example 1 | Good | Good |
| Example 2 | Good | Good |
| Example 3 | Good | Good |
| Example 4 | Good | Good |
| Example 5 | Good | Good |
| Example 6 | Good | Good |
| Example 7 | Good | Good |
| Example 8 | Good | Good |
| Example 9 | Good | Good |
| Comparative Example 1 | Not attached on to the island portions | Not proliferated on the island portions |
| Comparative Example 2 | Not attached | Not proliferated |

From the results of Examples 1 to 9, various shapes of the bed material for cell cultures coated with the temperature-responsive polymers to be illustrated by the present invention all enabled the conventional cell culture, and the states of cell attachability, cell proliferation and the like were equal to those of commercially available petri dishes. On the other hand, as shown in Comparative Examples 1 and 2, when part of the surface or the entire surface of the bed material for cell culture was coated with a large amount of a temperature-responsive polymer, the cell attachment to that portions could not be recognized, and thus such bed materials for cell culture were not suitable.

Examples 10 and 11

On the surface of the bed materials for cell culture as obtained in Examples 1 and 2, $10^7$ of rat hepatocyte was seeded and cultured at 37° C. for one day (Example 10, FIG. 1b) and for two days (Example 11)[medium used: a Williams E medium containing 10% bovine fetal serum (FCS), $10^{-8}$ M of dexamethasone, $10^{-7}$ M of insulin, 10 mM of nicotinamide, and furthermore 10 ng/ml of epithelial growth factor (EGF), 37° C. under 5% of $CO_2$]. It could be understood from FIG. 1b that the hepatocyte adhered and extended all over the surface.

Figure 1:
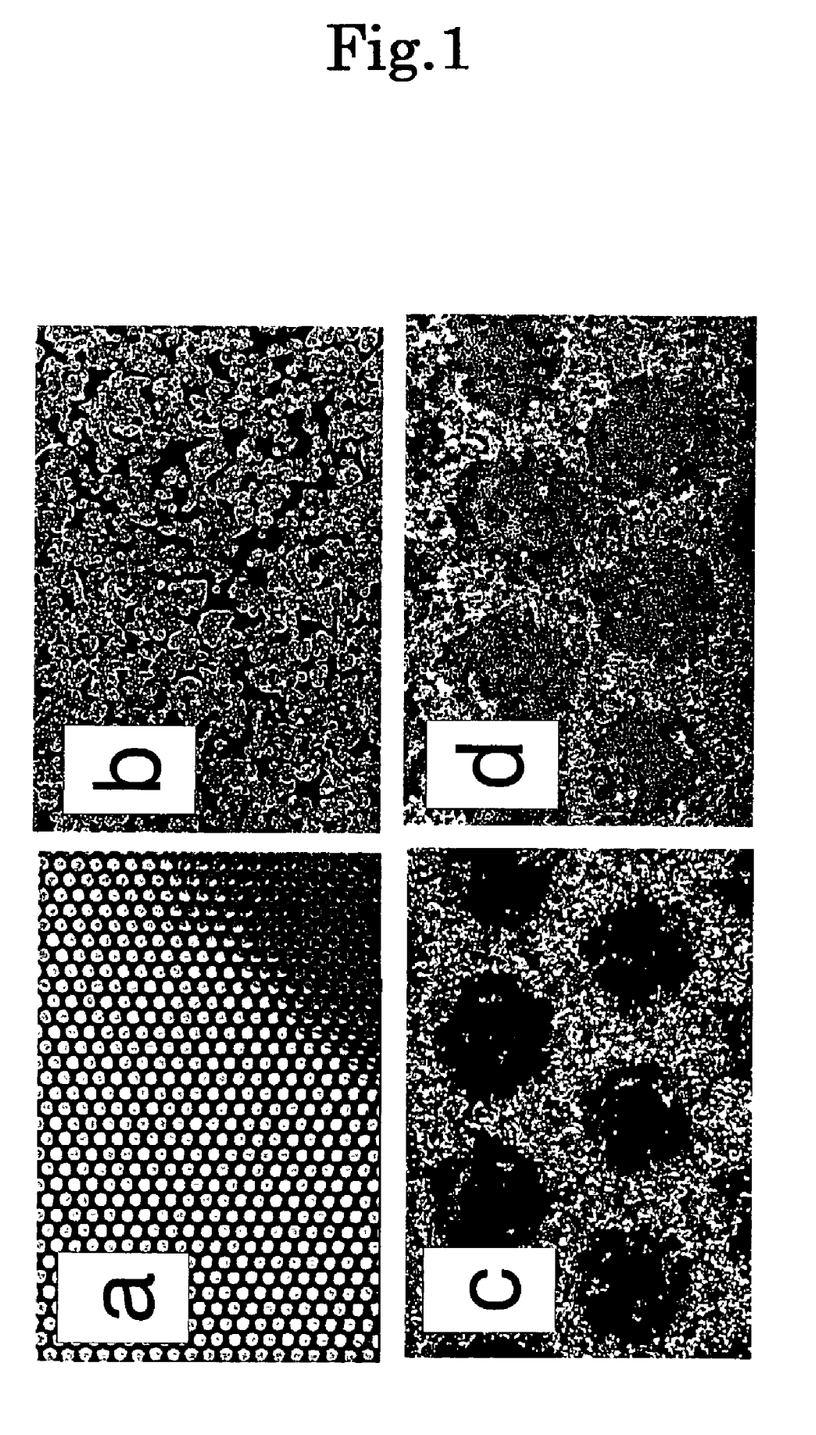
FIG. 1 shows microscopic photographs which explain the co-culture of hepatocyte with endothelial cells as described in Example 10.

After the culture, the obtained cells were incubated at 20° C. for two hours, and then the hepatocyte was detached only from the PIPAAm domain by pipetting (for example, in the case of Example 10, FIG. 1c). FIG. 1c shows that the cells were detached only from the temperature-responsive domain grafted with the PIPAAm.

Again, the temperature of the bed material for cell culture was returned to 37° C., and $10^7$ of rat vascular epithelial cells were seeded. The epithelial cells attached only to the cell-free PIPAAm domain. Subsequently, the co-culture was conducted at 37° C. for three days ([medium used: a cocktail medium obtained by mixing a Williams E medium containing 10% bovine fetal serum (FCS), $10^{-8}$ M of dexamethasone, $10^{-7}$ M of insulin, 10 mM of nicotinamide, and furthermore 10 ng/ml of epithelial growth factor (EGF) with a Dulbecco modified Eagle's medium (DMEM) at a 1:1 ratio, 37° C. under 5% of $CO_2$]. FIG. 1d is a view showing the proliferation state of each kind of cells after three days in Example 10. It could be understood from FIG. 1d that the hepatocyte and the endothelial cells could be stably co-cultured in accordance with the mask pattern.

The result of measuring the albumin productivity of the hepatocyte after the co-culture according to the conventional method is shown in Table 2.

Comparative Example 3

On a commercially available Falcon 3002 PETRI DISH (diameter: 6 cm), rat hepatocyte was cultured in the same manner as in Example 10. After the co-culture, the cells were incubated at 20° C. for two hours in the same manner as in Example 10, and then the cells on the substrate surface were tried to be detached by pipetting with difficulty. On the other hand, the culture of rat hepatocyte was continued on the same bed material for cell culture. The result of measuring the albumin productivity of the hepatocyte at that time is shown in Table 2.

Example 12

On the surface of the bed material for cell culture as obtained in Example 5, $10^7$ of rat hepatocyte was seeded and cultured at 37° C. for two days [medium used: a Williams E medium containing 5% bovine fetal serum (FCS), $10^{-8}$ M of dexamethasone, $10^{-7}$ M of insulin, 10 mM of nicotinamide, and furthermore 10 ng/ml of epithelial growth factor (EGF), 37° C. under 5% of $CO_2$]. After the culture, the obtained cells were incubated at 20° C. for 30 minutes, and then the hepatocyte was detached only from the domain coated with the PIPAAm in a larger amount by pipetting. Again, the temperature of the bed material for cell culture was returned to 37° C., and $10^7$ of rat vascular endothelial cells were seeded. The endothelial cells attached only to the hepatic parenchymal cell-detached, cell-free portions. Subsequently, the co-culture was conducted at 37° C. for three days [medium used: a cocktail medium obtained by mixing a Williams E medium containing 10% bovine fetal serum (FCS), $10^{-8}$ M of dexamethasone, $10^{-7}$ M of insulin, 10 mM of nicotinamide, and furthermore 10 ng/ml of epithelial growth factor (EGF) with a Dulbecco modified Eagle's medium (DMEM) containing 10% of bovine fetal serum (FCS) at a 1:1 ratio, 37° C. under 5% of $CO_2$]. The result of measuring the albumin productivity of the hepatocyte after the co-culture according to the conventional method is shown in Table 2.

Comparative Example 4

The entire surface of the FALCON 3002 PETRI DISH (diameter: 6 cm) was first coated with an N-isopropyl acrylamide polymer (PIPAAm) by the same method as in Example 5. Subsequently, a bed material for cell culture was obtained in the same manner as in Example 5 except that a 5% isopropyl alcohol solution of an N-isopropyl acrylamide monomer was further coated thereon in an amount of 0.2 ml. The amounts of the PIPAAm coated in the sea portion and the island portions were obtained in the same manner as in Examples 1 and 2, and found to be 1.6 µg/cm² and 1.65 µg/cm², respectively.

On the obtained the bed material for cell culture, hepatocyte was cultured in the same manner as in Example 12. After the culture, the cells were incubated at 20° C. for 30 minutes, and then when the hepatocyte was tried to be detached only from the domains coated with the PIPAAm in a larger amount by pipetting, the hepatic parenchymal present not only in the island portions but also in the sea portion were detached, and thus the bed material for cell culture was not suitable as the bed material for cell culture of the present invention.

Example 13

On the surface of the bed material for cell culture as obtained in Example 8, $10^7$ of rat hepatocytes was seeded and cultured at 37° C. for two days [medium used: a Williams E medium containing 5% bovine fetal serum (FCS), $10^{-8}$ M of dexamethasone, $10^{-7}$ M of insulin, 10 mM of nicotinamide, and furthermore 10 ng/ml of epithelial growth factor (EGF), 37° C. under 5% of $CO_2$]. After the culture, the obtained cells were incubated at 20° C. for one hour, and then the hepatocytes was detached only from the domain coated with the PIPAAm by pipetting. Again, the temperature of the bed material for cell culture was returned to 37° C., and $10^7$ of rat vascular endothelial cells were seeded. The endothelial cells attached only to the hepatic parenchymal cell-detached, cell-free portions. Subsequently, the co-culture was conducted at 37° C. for three days ([medium used: a cocktail medium by mixing a Williams E medium containing 10% bovine fetal serum (FCS), $10^{-8}$ M of dexamethasone, $10^{-7}$ M of insulin, 10 mM of nicotinamide, and furthermore 10 ng/ml of epithelial growth factor (EGF) with a Dulbecco modified Eagle's medium (DMEM) containing 10% of bovine fetal serum (FCS) at a 1:1 ratio, 37° C. under 5% of $CO_2$]. The result of measuring the albumin productivity of the hepatocyte after the co-culture according to the conventional method is shown in Table 2.

Comparative Example 5

A polymer was coated over the entire surface of the culture dish in the same manner as in Examples 5 and 6 except that 0.35 ml of a 30% isopropyl alcohol solution of an N-n-propyl methacrylamide monomer was coated on the above described commercially available PETRI DISH (diameter: 6 cm), and then a 20% isopropyl alcohol solution of an N-tetrahydrofurfuryl acrylamide monomer was further coated as in Example 5 to coat an N-tetrahydrofurfuryl acrylamide polymer in a larger amount on to the portions coated with the N-n-propyl methacrylamide polymer. After the irradiation, a bed material for cell culture was obtained through washing, drying and sterilization steps in the manner as in Examples 1 and 2. When the amounts of PIPAAm coated in the sea portion and the island portions were obtained and found to be 1.5 $\mu g/cm^2$ and 2.1 $\mu g/cm^2$, respectively.

On the obtained culture substrate material, hepatocyte was cultured in the manner as in Example 12. After the culture, the cells were incubated at 20° C. for 30 minutes and hepatocyte was tried to be detached only from the domain coated with PIPAAm in a larger amount by pipetting but the hepatocyte present not only in the island portions but also in the sea portion were detached, and thus the bed material for cell culture was not suitable as the bed material for cell culture of the present invention.

TABLE 2

| | Albumin Productivity (ng/h/$10^5$ cells) | | | | | |
|---|---|---|---|---|---|---|
| | After Co-culture For 1 Day | After Co-culture For 3 Days | After Co-culture For 7 Days | After Co-culture For 14 Days | After Co-culture For 21 Days | After Co-culture For 28 Days |
| Example 10 | 310 | 314 | 308 | 309 | 305 | 295 |
| Example 11 | 302 | 303 | 305 | 312 | 310 | 300 |
| Example 12 | 307 | 307 | 312 | 305 | 300 | 293 |
| Example 13 | 312 | 303 | 304 | 309 | 308 | 295 |
| Comparative Example 3 | 238 | 118 | 12 | 0 | 0 | 0 |

From the results of Examples 10 to 13, it would be understood that according to the co-culture method to be illustrated in the present invention, the activity of the hepatocyte which could not be retained only for several days by the conventional technique (Comparative Example 3) can be retained over such an extremely long period of time as 4 weeks.

Example 14

On the surface of the bed material for cell culture as obtained in Example 7, $10^7$ of rat intracerebral nerve cells were seeded and cultured (medium used: a 1:1 mixed medium of MEM and Ham's F-12 containing 15 µg/ml human transferring, 5 mg/ml pig insulin, 20 nM of progesterone, 30 nM of sodium selenite, 100 µM of putrescine, 50µ unit/ml of streptomycin, and 50µ unit/ml of penicillin, 30° C. under 5% of $CO_2$) at 30° C. for three days according to the conventional method to first allow the rat intracerebral nerve cells to proliferate on the N-n-propyl acrylamide polymer in the form of lines. After the culture, the temperature of the bed material for cell culture was raised to 37° C. and $10^7$ of rat glial cells were seeded and cultured [medium used: a 1:1 mixed cocktail medium obtained by mixing the above medium in which the nerve cells had been cultured with a 1:1 mixed medium of DMEM and Ham's F-12 containing 10% of bovine fetal serum (FCS), 37° C. under 5% of $CO_2$]. The glial cells attached to the nerve cell-free portions and proliferated in the form of lines. Subsequently, the co-culture was conducted at 37° C. for three days.

As the result, the nerve cells and the glial cells could be allowed to proliferate in the form of lines, respectively, or without the proliferation of either kind of the cells in a larger amount or without the mixed proliferation of both kinds of cells with each other.

From this fact, in accordance with the co-culture method illustrated in the present invention by using the bed material for cell culture of the present invention, the culture of nerve cell and glial cells in the form of a pattern which has been difficult in the past has become possible, and the co-cultured cells are useful as the biochip.

Examples 15 and 16

The hepatocyte and the vascular endothelial cells as co-cultured in Examples 12 and 13 were incubated at 20° C. for two hours together with the bed material for cell culture, and all cells were detached by pipetting (in Example 15 and Example .16, respectively). According to the conven-tional method, the albumin productivity of the detached cells was measured and the results are shown in Table 3.

TABLE 3

| | Albumin Productivity (ng/h/$10^5$ cells) | | | | | |
|---|---|---|---|---|---|---|
| | After Co-culture For 1 Day | After Co-culture For 3 Days | After Co-culture For 7 Days | After Co-culture For 14 Days | After Co-culture For 21 Days | After Co-culture For 28 Days |
| Example 15 | 521 | 524 | 518 | 515 | 517 | 523 |
| Example 16 | 527 | 523 | 521 | 529 | 525 | 528 |

From the results of Examples 15 and 16, it would be understood that according to the co-culture method to be illustrated in the invention of this application, the activity of the hepatocyte which could not be retained only for several days by the conventional technique (Comparative Example 4) can be retained over such an extremely long period of time as 4 weeks. In addition, it would be understood that the activity can further be enhanced than the activity as shown in Examples 10 to 13.

Example 17

On the surface of the bed material for cell culture as obtained in Example 5, $10^6$ of rat alveolar epithelial cells (15% of the total number of cells being fibroblasts present as the mixture) seeded and cultured [medium used: a cocktail medium obtained by mixing a DMEM containing 2% of bovine fetal serum (FCS), 10 µg/ml of insulin, 100 ng/ml of cholera toxin, 5 µg/ml of cortisol with a Ham's F-12 at a 1:1 ratio, 37° C. under 5% of $CO_2$] at 37° C. for two days according to the conventional method to allow cells to proliferate over the entire surface of the bed material for cell culture. After the culture, the obtained cells were incubated at 20° C. for two hours, and then all cells were detached from the substrate surface by pipetting. Subsequently, the above described medium of 37° C. was introduced into the bed material for cell culture and the previously detached cell sheet was returned thereto.

Figure 2:
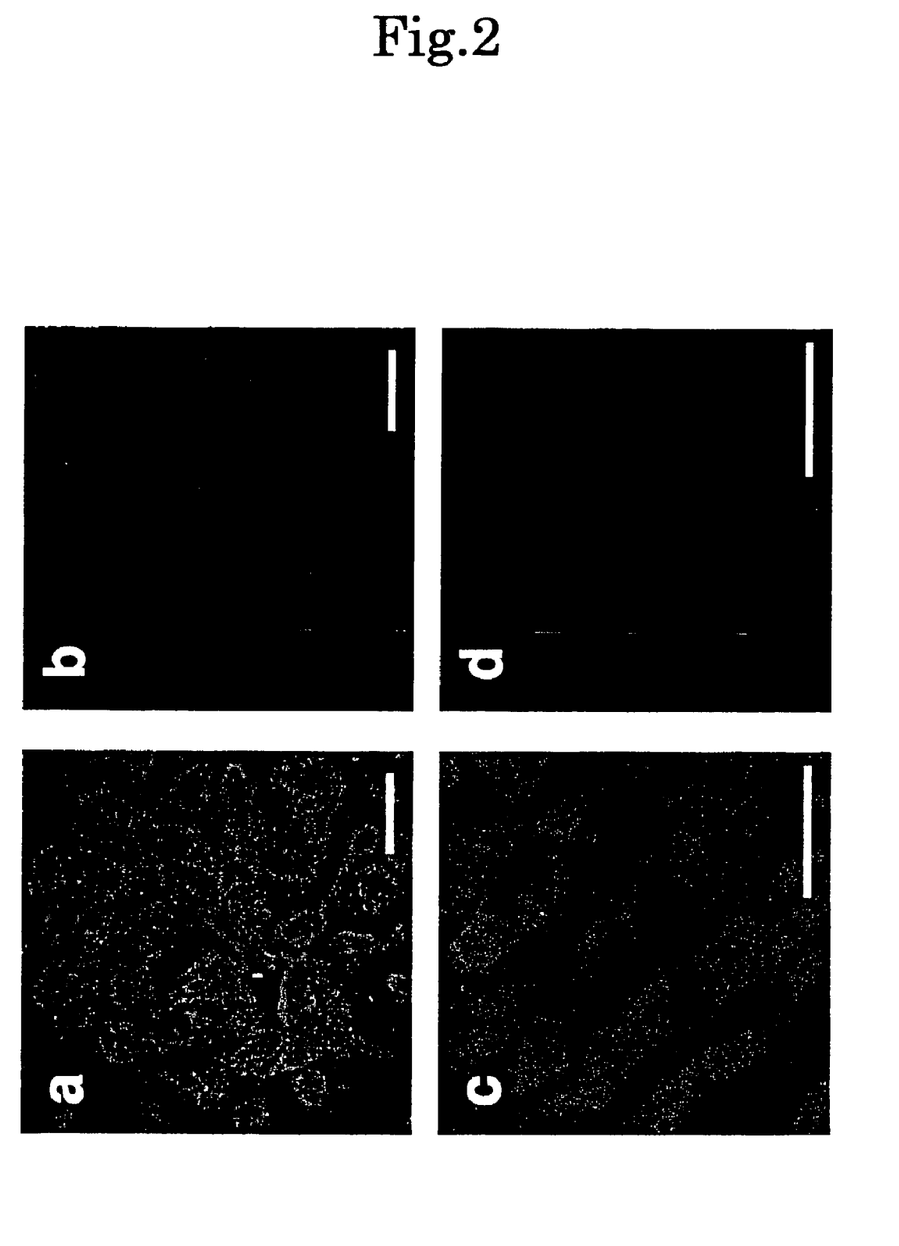
FIG. 2 shows microscopic photographs when the surfactant protein to be secreted from the alveolar epithelial cells was subjected to fluorescence stain by the conventional method in order to explain the co-culture of alveolar epithelial cells with fibroblasts as described in Example 17.
Figure 3:
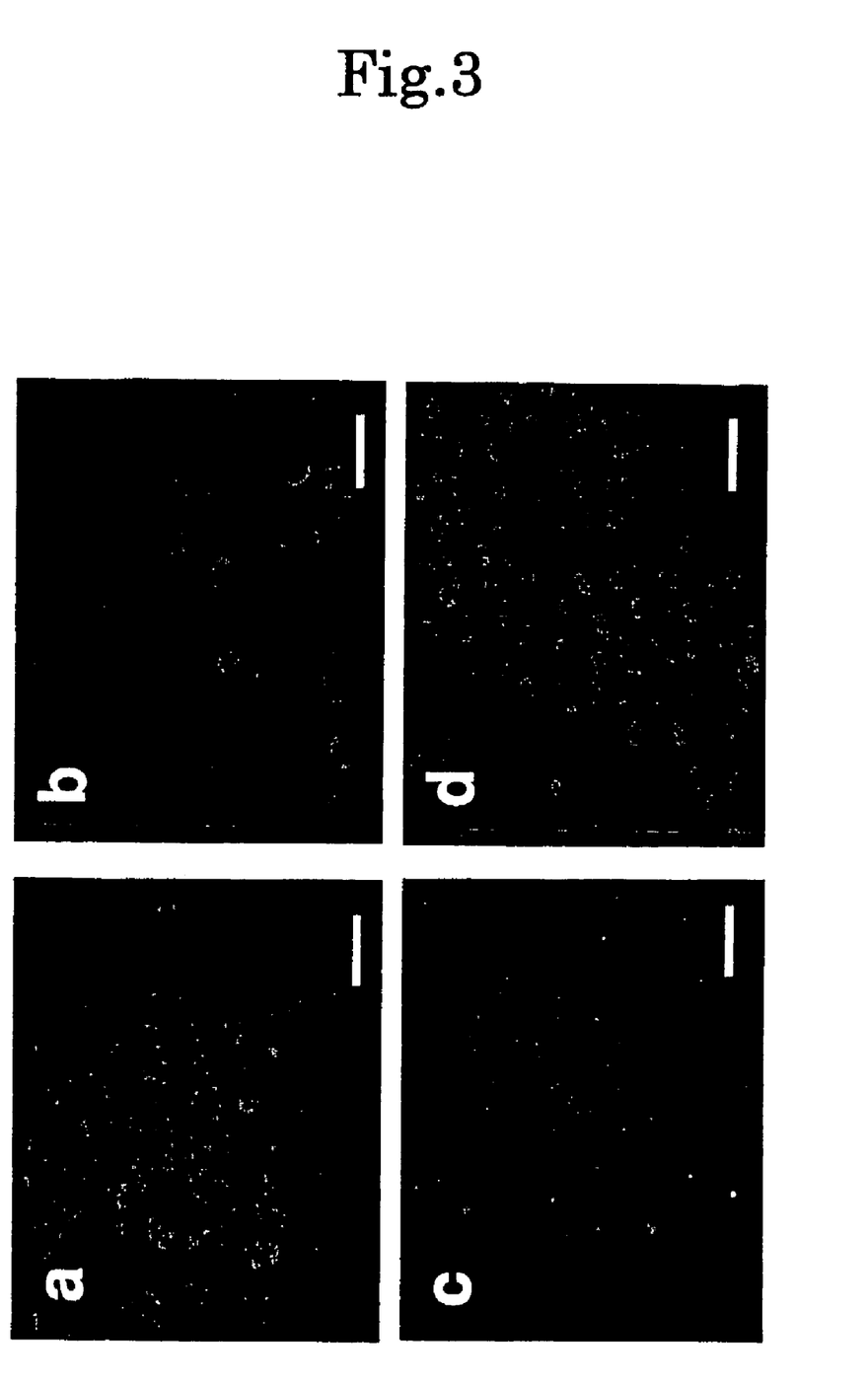
FIG. 3 shows microscopic photographs which explain the co-culture of alveolar epithelial cells with fibroblasts as described in Example 17 as in FIG. 2.
Figure 4:
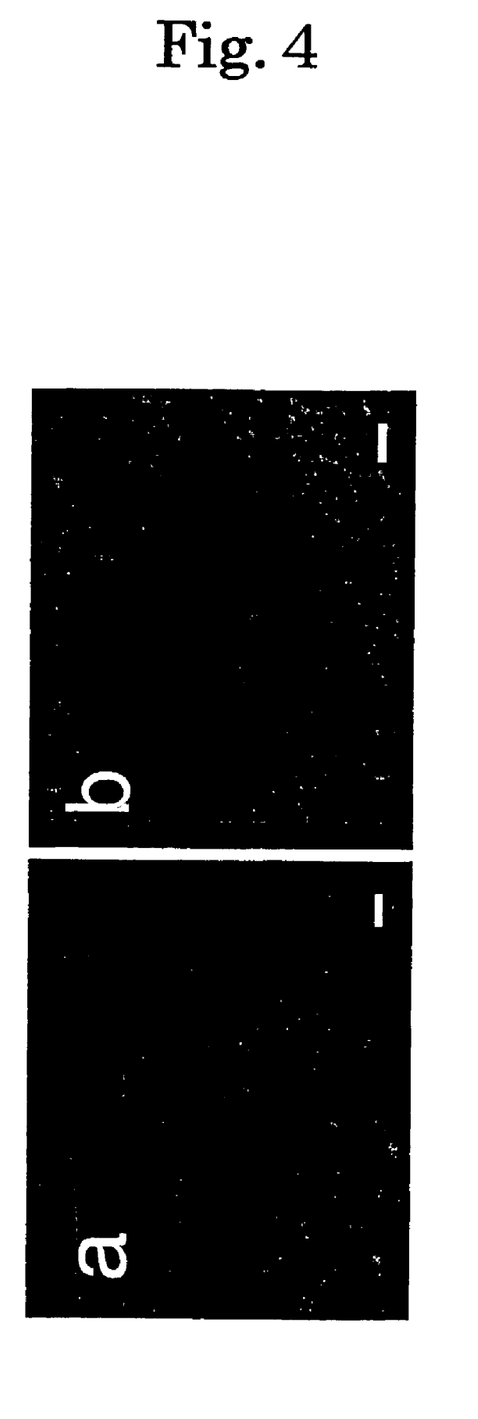
FIG. 4 shows microscopic photographs when a specific sugar chain of the surface layer of the alveolar epithelial cells was subjected to fluorescence stain in order to explain the co-culture of alveolar epithelial cells with fibroblasts as described in Example 17 as in FIG. 2.

The obtained results are shown in FIGS. 2 to 4. FIGS. 2 and 3 are the results of subjecting the surfactant protein to be secreted from the alveolar epithelial cells to fluorescence stain according to the conventional method. It could be understood that before detaching the alveolar epithelial cells in which fibroblasts were mixedly present from the bed material for cell culture (after culturing for 13 days, FIG. 2a), the surfactant protein had been secreted from the alveolar cells and when the co-culture as such was continued for 22 days, the amount of secretion was sharply decreased. On the other hand, when the cells were detached after culturing for 13 days by the above described method and allowed to reattach on to the bed material for cell culture, it could be understood that when the cells were detached and further cultured even for 30 days (FIG. 3a) or for 60 days (FIG. 3c), the surfactant protein had been secreted. From this fact, according to the co-culture method illustrated by the present invention by using the bed material for cell culture of the present invention, the maintenance of the activity of the alveolar epithelial cell over a long period of time which has been difficult in the past has now been made possible. Furthermore, this has been clear also from the expression of a specific sugar chain of the surface layer of the alveolar epithelial cells. FIG. 4a shows the result of the fluorescence stain of the sugar chain of the surface layer of the alveolar epithelial cells after culturing for 13 days according to the conventional method. FIG. 4b shows the result when the cells was detached and subsequently allowed to reattach on to the bed material for cell culture, and it could be understood that the alveolar epithelial cells were clearly activated.

INDUSTRIAL APPLICABILITY

Compared to the conventional bed material for cell culture, the bed material for cell culture of the present invention can be utilized in various culture methods which can control the type, amount, coating area and the like of each polymer to be coated on the material surface. As the result, even in the culture of cells such as hepatocyte, alveolar epithelial cells and nerve cells whose activity has been very difficult to continuously maintain high in the conventional technology, the maintenance of a sufficient activity over a long period of time has been enabled. Accordingly, the bed material for cell culture, the method for the co-culture of cells with the use of the material and the method for preparing a cell sheet according to the present invention are very useful inventions in the fields of medicine, safety evaluation, biology and the like such as cell technology, genetic technology and medical engineering.

The invention claimed is:

1. A bed material for cell culture having an array of one or more domains of domain A coated with a temperature-responsive polymer and one or more domains of domain B composed of any one or a combination of any two or three of (1) a domain coated with a polymer having high affinity with cells, (2) a domain coated with the temperature-responsive polymer in an amount different from the amount of the temperature-responsive polymer of domain A, with the difference in the amount coated between domains A and B being at least 0.10 µg/cm² or more, and (3) a domain coated with a polymer which responds to a temperature different from the temperature to which domain A responds.

2. The bed material for cell culture of claim 1, wherein at least one temperature-responsive polymer is poly(N-isopropyl acrylamide).

3. A method for the co-culture of cells using the bed material for cell culture of claim 1, which comprises seeding and culturing cells on both of domains A and B of the surface of the bed material, detaching and removing the cells on either domain A or domain B by changing a temperature, thereafter seeding and culturing a different kind of cells on the cell free domain thus culturing different kinds of cells on the same sheet, and detaching and removing each of the different kinds of cells from the surface of the bed material by changing a temperature of the sheet.

4. The method of claim 3, which comprises first culturing cells on the surface of the bed material for cell culture of claim 1 whose domain B has not entirely been coated with a temperature-responsive polymer for a specified period of time, detaching and removing the entire cells or part thereof on the temperature-responsive polymer, and then seeding and culturing a different kind of cells or further repeating these procedures.

5. The method of claim 3, which comprises first culturing cells on the surface of the bed material for cell culture of claim 1 whose domain B has been entirely coated with a temperature-responsive polymer for a specified period of time, then detaching and removing part of the cells or part thereof on the temperature-responsive polymer, and subsequently seeding a different kind of cells to proliferate or further repeating these procedures.

6. The method of claim 3, which comprises, on the surface of the bed material for cell culture of claim 1 whose domain B has been entirely or partially coated with a temperature-responsive polymer different from the temperature-responsive polymer of domain A, first allowing cells to attach on to the polymer of either domain A or domain B to proliferate, and then allowing a different kind of cells to attach on to the other polymer to culture said different kind of cells.

7. A method for the co-culture of cells which comprises seeding and culturing a plurality of kinds of cells on the surface of the bed material for cell culture of claim 1 from the beginning of the culture, then detaching the entire cells or part thereof and allowing the detached cells to reattach on to the bed material for cell culture or further repeating these procedures.

8. The method for the co-culture of cells of claim 3, wherein the combination of cells for the co-culture is a combination of hepatocyte with endothelial cells, alveolar epithelial cells with fibroblasts or nerve cells with glia cells.

9. A co-cultured cell sheet to be obtained by detaching the cells on the surface of the substrate obtainable by the method for the co-culture of cells of claim 3.

* * * * *